United States Patent
Barrett et al.

(10) Patent No.: US 6,622,047 B2
(45) Date of Patent: Sep. 16, 2003

(54) TREATMENT OF NEUROPSYCHIATRIC DISORDERS BY NEAR-DIAPHRAGMATIC NERVE STIMULATION

(75) Inventors: Burke T. Barrett, Houston, TX (US); Reese S. Terry, Jr., Houston, TX (US)

(73) Assignee: Cyberonics, Inc., Houston, TX (US)

(*) Notice: Subject to any disclaimer, the term of this patent is extended or adjusted under 35 U.S.C. 154(b) by 0 days.

(21) Appl. No.: 09/917,603

(22) Filed: Jul. 28, 2001

(65) Prior Publication Data

US 2003/0023282 A1 Jan. 30, 2003

(51) Int. Cl.[7] .................................................. A61N 1/18
(52) U.S. Cl. ......................................................... 607/45
(58) Field of Search ................................ 607/2, 44, 45, 607/72, 118

(56) References Cited

U.S. PATENT DOCUMENTS

| | | |
|---|---|---|
| 4,702,254 A | 10/1987 | Zabara |
| 4,867,164 A | 9/1989 | Zabara |
| 5,025,807 A | 6/1991 | Zabara |
| 5,299,569 A * | 4/1994 | Wernicke et al. |

OTHER PUBLICATIONS

Lahmeyer et al., "Biologic Markers in Borderline Personality Disorder: A Review," *J. Clin. Psych.* (1989) 50(6):217–225.

Rush et al., "A Journal of Psychiatric Neuroscience," *Biological Psychiatry*, Feb. 2000.

* cited by examiner

*Primary Examiner*—Scott M. Getzow
(74) *Attorney, Agent, or Firm*—Blank Rome LLP

(57) ABSTRACT

A method and apparatus for treating patients with neuropsychiatric disorder includes unilaterally or bilaterally stimulating one or both of the left and right branches of a patient's vagus nerve directly or indirectly with an electrical pulse signal generated by an implantable neurostimulator with at least one operatively coupled nerve electrode to apply the pulse signal to the selected nerve branch at a location in the vicinity of the patient's diaphragm, either slightly above or slightly below the diaphragm. The implantable neurostimulator is programmable to enable physician programming of electrical and timing parameters of the pulse signal, to generate the desired therapy regimen for alleviating the disorder. Patient activation of the device is permitted in the case of treating a neuropsychiatric disorder such as depression, where the patient is able to sense a symptom of a disorder.

22 Claims, 1 Drawing Sheet

TREATMENT OF NEUROPSYCHIATRIC DISORDERS BY NEAR-DIAPHRAGMATIC NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating patients with neuropsychiatric disorders by application of such signals to the vagus nerve or other suitable cranial nerve, using an implantable neurostimulator. Specifically, the invention is directed toward treating the symptoms of neuropsychiatric disorders such as schizophrenia, depression, and borderline personality disorder, by selective modulation of vagus nerve activity.

Although schizophrenia was initially thought to have only psychological origins, more recent psychobiology and psychopharmacology findings have indicated that the illness is primarily organic in nature. Electrophysiologic studies of patients with schizophrenia have supported an organic etiology. Although not entirely consistent, electroencephalogram (EEG) studies have tended to reveal abnormalities in these patients. Also, some parallels have been found between schizophrenia and epilepsy.

Developments in psychobiology and psychopharmacology have also provided considerable evidence that major depressive disorder and bipolar depression are biological rather than psychological diseases. The conclusion that depression has a biological basis is also supported by numerous electrophysiological and endocrine studies. Deficiency of brain neurotransmitters has been associated with depression. In particular, abnormally low concentrations of the neurotransmitter serotonin and its metabolites and norepinephrine have been found in depressed patients. Several serotonin uptake inhibitors, which increase the amount of serotonin at the synapse have been shown to be effective antidepressants. Iincreased activity of the vagus nerve has been postulated to be associated with release of increased amounts of serotonin and norepinephrine in the brain.

Borderline personality disorder is a poorly understood, but recognized psychiatric disorder which seems to have some overlap of schizophrenia and depression. Patients tend to be poorly functional without florid psychosis or overt depression. Lahmeyer et al. reported, in *J. Clin. Psych.* (1989) 50(6):217–225, that sleep architecture in patients with borderline personality disorder is disturbed in that REM latency is decreased and REM density is increased. This was found to be particularly true if patients suffered coexisting depression, a history of affective illness or a family history of psychopathology. Sleep abnormalities were reported to appear similar to those seen in affective disorders.

It is an object of the present invention to apply the techniques of selective modulation of vagus nerve electrical activity, using a neurostimulator device which may be implantable, or used external to the body with only a small portion of the circuitry implanted or with only the nerve electrode(s) and associated lead(s) implanted percutaneously in the body, to the treatment of neuropsychiatric disorders including schizophrenia, depression, and borderline personality disorder, as well as other neuropsychiatric disorders as defined in the Diagnostic and Statistical Manual of Mental Disorders.

In U.S. Pat. No. 5,299,569 (sometimes referred to herein as "the '569 patent"), assigned to the same assignee as the present application, Wernicke et al disclosed methods and devices for treating and controlling certain neuropsychiatric disorders by selective stimulation of the vagus nerve. A neurostimulator which is preferably but not necessarily implantable selectively applies the therapy to treat the specific neuropsychiatric disorder such as schizophrenia, depression, borderline personality disorder, or other related disorder. The therapy is delivered in a manner to stimulate or modulate the vagal activity of the patient in a predetermined manner to treat and relieve the symptoms of the disorder, although it may not be effective in alleviating the underlying root cause of the disorder. The neurostimulator is programmed by the attending physician to generate a pulsed electrical signal that provides the desired therapeutic modality for treatment.

In the '569 patent, the applicants reported their conclusion that vagal stimulation can be effective for treating schizophrenia, for example. One observation toward that conclusion is that fast desynchronous (beta) activity and paroxysmal (synchronous) activity of the EEG have both been reported in studies of this disorder. At some stimulation parameters, vagal stimulation will synchronize the EEG, with a resultant beneficial effect on treatment of the disorder where increased beta wave activity is present. A second observation is the apparent relationship between schizophrenia and temporal lobe epilepsy. The temporal lobes are part of the limbic system, which they postulated is malfunctioning in patients with schizophrenia. Vagal stimulation can suppress temporal (complex partial) seizures, which are generated in the limbic system. The structures of this system are interconnected, and the beneficial effect of vagal stimulation seen in the temporal lobes may be transmitted to other brain structures, leading to a similar effect on schizophrenia. In this case, the abnormality being treated is a synchronous paroxysmal (epileptiform) discharge, and the therapy is designed to desynchronize the EEG.

In the treatment, different signal parameters and threshold curves are used to activate the various fibers of the patient's vagus nerve for selective modulation thereof by appropriately setting pulse width and amplitude of the electrical signal to be delivered by the neurostimulator to the patient's vagus nerve. It was recommended that to increase desynchronous activity of the EEG for treatment of a neuropsychiatric disorder, it would be prudent to use a short pulse train for the stimulus because the fibers could become refractory to the stimulation within a relatively short time interval. Then, after a suitable recovery period, another short pulse train may be applied to achieve further treatment. The precise pattern to be used, including the length of the time intervals on and off, depends upon and is adjusted to the individual patient and the particular disorder being treated.

The basic stimulation strategy called for modulating the activity of a number of brain structures, including the limbic system, the reticular formation, and the hippocampus through selective stimulation of the vagus nerve, which projects directly or indirectly to these brain structures. The strategy may be implemented by circadian programming to automatically activate the stimulus generator to continuously, periodically or intermittently generate an electrical signal appropriate for application to the patient's vagus nerve to modulate its activity and that of these brain structures. In another aspect, the treatment is carried out by applying the selectively modulating electrical signals to the patient's vagus nerve in response to the occurrence of one or more predetermined detectable events.

In the case of depression, vagal stimulation may be used to alter sleep state architecture as a modality that may produce a beneficial antidepressant effect. Certain stimulation parameters for the vagus nerve may produce synchronization of brain activity which leads to the biochemical changes required to relieve depression, without causing seizures. It is also noted in the '569 patent that vagal stimulation may be effective in the treatment of borderline personality disorder, at least because of the abnormalities in sleep architecture attendant with such disorders and the capability of vagal stimulation to alter sleep states. Recently, left cervical vagus nerve stimulation has been shown to have antidepressant effects in the treatment of patients with major depression and bipolar disorder (Rush et al, *Biological Psychiatry*, February, 2000).

Methods and apparatus for treating and controlling neuropsychiatric disorders according to the '569 patent involves applying electrical stimuli to the patient's vagus nerve or other appropriate cranial nerve, which may activate a specific group of fibers from among all of the fiber groups of the selected nerve(s), and selectively synchronize or desynchronize the patient's EEG and/or vary REM activity according to the specific nature of the disorder, and/or alter brain serotonin concentrations. Also, it was contemplated that the methods of treating and controlling neuropsychiatric disorders could be implemented by sensing a symptom of the disorder or the occurrence of a predetermined detectable event and thereafter automatically or manually effecting modulation of vagal activity through the application of preselected stimuli to the patient's vagus nerve to suppress the disorder. For example, by means of implanted surface or depth electrodes specific characteristics of the patient's EEG may be sensed for triggering the therapy. Alternatively, eye movement sensing electrodes may be implanted at or near the outer periphery of each eye socket to sense muscle movement or actual eye movement, and electrically connected via electrical leads to a sense signal analysis circuit of neurostimulator for rapid eye movement (REM) detection in a pattern indicative of the disorder to be treated. But since these sensing techniques involve complex and delicate electrode/lead implantation procedures, and in some instances a need for spectral analysis and/or programmable spectral or pattern recognition, it was preferred that the treatment be applied continuously, periodically or intermittently or in accordance with the patient's circadian rhythm. In the preferred implementation of the '569 patent, the electrode assembly is surgically implanted on the vagus nerve in a cervical location, in the patient's neck. The nerve electrodes may be wrapped about the vagus nerve, and the assembly secured to the nerve by a spiral anchoring tether.

It is a principal aim of the present invention to provide a new technique for treating neuropsychiatric disorders using stimulation of a suitable cranial nerve, especially the vagus nerve.

SUMMARY OF THE INVENTION

According to the present invention, a method of treating patients suffering from neuropsychiatric disorder, such as but not limited to schizophrenia, depression, or borderline personality disorder, comprises unilateral or bilateral stimulation of the left and right vagi in the immediate vicinity of the patient's diaphragm. Preferably, the treatment is administered at either a supra-diaphragmatic position (i.e., above the diaphragm) or sub-diaphragmatic position (i.e., below the diaphragm) in the ventral cavity. The stimulating electrical signal is preferably applied to the vagus two to three inches above or below the diaphragm, and may be applied either synchronously or asynchronously to both the right and left branches, preferably in the form of a series of pulses applied intermittently to both branches according to a predetermined on/off duty cycle. The intermittent application is preferably chronic, rather than acute. However, continuous application or acute application by bilateral stimulation of the right and left vagi or unilateral stimulation of either branch of the nerve is also contemplated.

Automatic delivery of bilateral intermittent stimulation is preferred, but alternatively in the case of certain neuropsychiatric disorders application of the stimulating electrical signal to the right and left vagi may be controlled by an external commencement signal produced by the patient's placement of an external magnet or use of other appropriate device or signaling mechanism in proximity to the location of the implanted device.

Preferably, the same stimulating electrical signal is applied to both the right and left vagi, but as an alternative, a stimulating electrical signal might be applied to the right vagus which is different from the stimulating electrical signal applied to the left vagus. And although two separate nerve stimulator generators may be implanted for stimulating the left and right vagi, respectively, as an alternative a single nerve stimulator generator may be implanted for bilateral stimulation if the same signal is to be applied to both the left and right branches of the vagus nerve, whether delivered synchronously or asynchronously to the vagi.

Preferably, the current magnitude of the stimulating signal is programmed to be less than about 6 mA, to be below the retching level of the patient as determined by the implanting physician at the time the implant procedure is performed. This is desirable to avoid patient nausea during periods of vagus nerve stimulation. Preferably, the pulse width is set to a value not exceeding about 500 microseconds ($\mu$s), the pulse repetition frequency is set at about 20–30 Hertz (Hz), the VNS regimen follows alternating periods of stimulation and no stimulation, with the second period about 1.8 to 6 times the length of the first period in the alternating sequence (i.e., the on/off duty cycle is 1:1.8 to 1:6).

Alternative techniques include indirect stimulation of the vagus, either bilaterally or unilaterally, at a location near one or both branches of the nerve or elsewhere, which has the effect of stimulating the vagus nerve as well. This may be accomplished through afferents or efferents, for example. It is also contemplated that direct or indirect unilateral or bilateral stimulation, applied in the vicinity of the patient's diaphragm, of one or more of the other cranial nerves of suitable sensory, motor or mixed fiber types may be effective in treating neuropsychiatric disorder, as an alternative to vagus nerve stimulation.

Some differences may be observed from stimulator to stimulator in magnitude of current in the pulses of the stimulation signal, and may be attributable to things such as patient impedance, variation of the vagus nerve from right to left or between patients, and variation in contact between the vagus and the electrode implanted thereon from implant to implant.

BRIEF DESCRIPTION OF THE DRAWINGS

The above and still further aims, objectives, aspects, features and attendant advantages of the present invention will be better understood from a consideration of the following detailed description of a presently contemplated best mode of practicing the invention, by reference to a preferred exemplary method and embodiment thereof, taken in conjunction with the accompanying Figures of drawing, in which.

DESCRIPTION OF THE PRESENTLY CONTEMPLATED BEST MODE AND ALTERNATIVE MODES OF PRACTICE

A generally suitable form of neurostimulator for use in the apparatus and method of the present invention is disclosed, for example, in U.S. Pat. No. 5,154,172, assigned to the same assignee as the instant application (the device also referred to from time to time herein as a NeuroCybernetic Prosthesis or NCP device (NCP is a trademark of Cyberonics, Inc. of Houston, Tex., the assignee)). Certain parameters of the electrical stimuli generated by the neurostimulator are programmable, preferably by means of an external programmer (not shown) in a conventional manner for implantable electrical medical devices.

Figure 1:
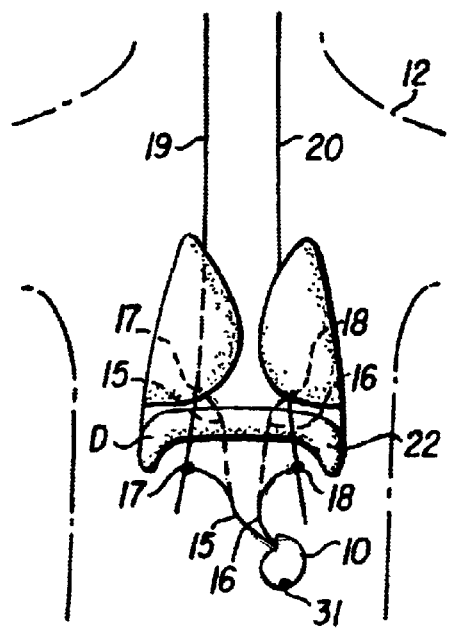
FIG. 1 is a simplified partial front view of a patient (in phantom) having an implanted neurostimulator for generating the desired signal stimuli which are applied directly and bilaterally at a near-diaphragmatic location to the right and left branches of the patient's vagus via an implanted lead/ nerve electrode system electrically connected to the neurostimulator.

Referring to FIG. 1, the neurostimulator (sometimes referred to herein as stimulus generator, signal generator, pulse generator, or simply the device), identified in the drawing by reference number 10 is implanted in a patient 12, preferably in the abdominal region, for example, via a left laporotomy incision. For the preferred implementation and method of direct bilateral stimulation, lead-electrode pair 15, 16 is also implanted during the procedure, and the proximal end(s) of the lead(s) electrically connected to the neurostimulator. The lead-electrode may be of a standard bipolar lead nerve electrode type available from Cyberonics, Inc.

It will be understood that the overall device generally is required to be approved or sanctioned by government authority for marketing as a medical device implantable in a patient together with electrode means to treat the involuntary movement disorder by stimulation of a selected cranial nerve (e.g., the vagus nerve) of the patient. The treatment is performed using a predetermined sequence of electrical impulses generated by the pulse generator and applied to the selected cranial nerve at a location in a range, preferably, from about two to about three inches above or below the patient's diaphragm, for alleviating symptoms of the neuropsychiatric disorder in the patient. In the United States, the government agency for sanctioning such marketing and use is the U.S. Food and Drug Administration (FDA), while in other countries, sanctioning is typically handled by the counterpart of the FDA for the respective country. Thus, in the United States the same device may not be marketed or used to administer therapy to treat two different diseases or disorders absent FDA approval of the device for both.

According to the preferred method of the invention, the nerve electrodes 17, 18 are implanted on the right and left branches 19, 20, respectively, of the patient's vagus nerve at either a supra-diaphragmatic or sub-diaphragmatic location. The nerve electrodes are equipped with tethers for maintaining each electrode in place without undue stress on the coupling of the electrode onto the nerve itself. Preferably, the location of this coupling is approximately two to three inches above or below the patient's diaphragm 22 for each branch 19, 20.

Neurostimulator 10 generates electrical stimuli in the form of electrical impulses according to a programmed regimen for bilateral stimulation of the right and left branches of the vagus. During the implant procedure, the physician checks the current level of the pulsed signal to ascertain that the current is adjusted to a magnitude at least slightly below the retching threshold of the patient. Typically, if this level is programmed to a value less than approximately 6 mA, the patient does not experience retching attributable to the VNS although variations may be observed from patient to patient. In any event, the maximum amplitude of the current should be adjusted accordingly until an absence of retching is observed, with a suitable safety margin. The retching threshold may change noticeably with time over a course of days after implantation, so the level should be checked especially in the first few days after implantation to determine whether any adjustment is necessary to maintain an effective regimen.

The bilateral stimulation regimen of the VNS preferably employs an intermittent pattern of a period in which a repeating series of pulses is generated for stimulating the nerve, followed by a period in which no pulses are generated. The on/off duty cycle of these alternating periods of stimulation and no stimulation preferably has a ratio in which the off time is approximately 1.8 to 6 times the length of the on time. Nominally, the width of each pulse is set to a value not greater than about 500 $\mu$s, and the pulse repetition frequency is programmed to be in a range of about 20 to 30 Hz. The electrical and timing parameters of the stimulating signal used for VNS as described herein for the preferred embodiment will be understood to be merely exemplary and not as constituting limitations on the scope of the invention.

The intermittent aspect of the bilateral stimulation resides in applying the stimuli according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective in treating neuropsychiatric disorders.

Figure 2:
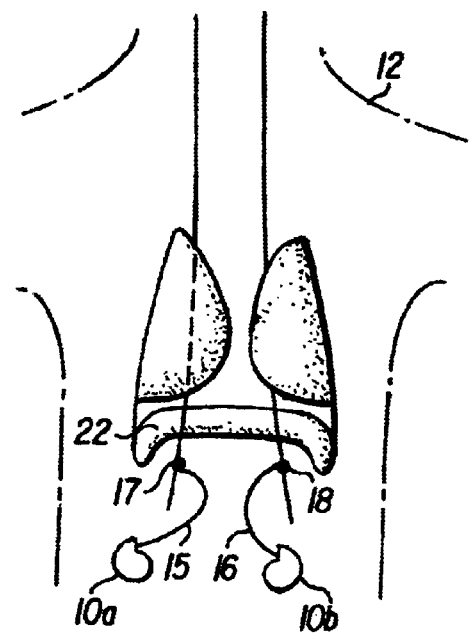
FIG. 2 is a simplified partial front view of a patient similar to that of FIG. 1, but in which a pair of implanted neurostimulators is used for generating the desired signal stimuli.

Also, as shown in FIG. 2, dual implanted NCP devices 10a and 10b may be used as the pulse generators, one supplying the right vagus and the other the left vagus to provide the bilateral stimulation. At least slightly different stimulation for each branch may be effective as well. Use of implanted stimulators for performing the method of the invention is preferred, but treatment may conceivably be administered using external stimulation equipment on an out-patient basis, albeit only somewhat less confining than complete hospitalization. Implantation of one or more neurostimulators, of course, allows the patient to be completely ambulatory, so that normal daily routine activities including on the job performance is unaffected.

Figure 3:
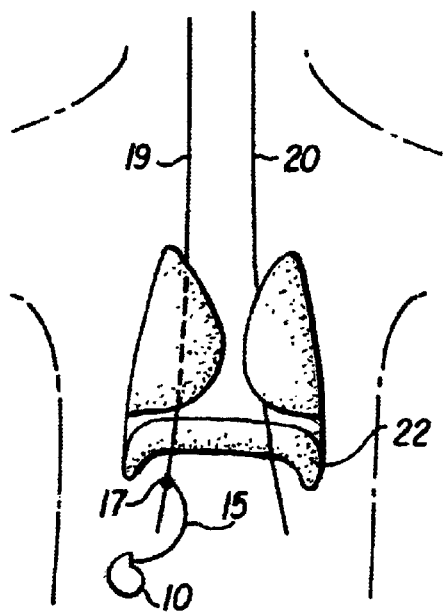
FIG. 3 is a simplified partial front view of a patient in which an implanted neurostimulator and associated electrode is used for unilateral stimulation of only one branch of the vagus nerve at the near-diaphragmatic location.

The desired stimulation of the patient's vagus nerve may also be achieved by performing unilateral supra-diaphragmatic or sub-diaphragmatic stimulation of either the left branch or the right branch of the vagus nerve, as shown in FIG. 3. A single neurostimulator 10 is implanted together with a lead 15 and associated nerve electrode 17. The nerve electrode 17 is implanted on either the right branch 19 or the left branch 20 of the nerve, preferably in a location in a range of from about two to about three inches above or below the patient's diaphragm 22. The electrical signal stimuli are the same as described above.

Figure 4:
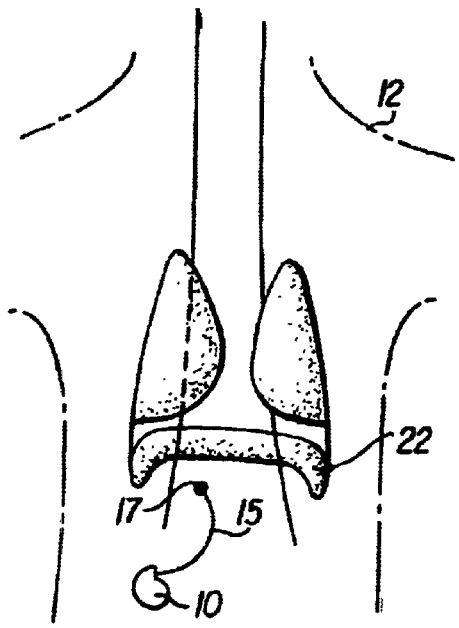
FIG. 4 is a simplified partial front view of a patient in which the signal stimuli are applied at a portion of the nervous system remote from the vagus nerve, for indirect stimulation of the vagus nerve at the near-diaphragmatic location.

In a technique illustrated in FIG. 4, the signal stimuli are applied at a portion of the nervous system remote from the vagus nerve, for indirect stimulation of the vagus nerve in the vicinity of the diaphragmatic location. Here, at least one signal generator 10 is implanted together with one or more electrodes 17 subsequently operatively coupled to the generator via lead 15 for generating and applying the electrical signal internally to a portion of the patient's nervous system other than the vagus nerve, to provide indirect stimulation of the vagus nerve in the vicinity of the desired location. Alternatively, the electrical signal stimulus may be applied non-invasively to a portion of the patient's nervous system for indirect stimulation of the vagus nerve at the diaphragmatic location.

In treating schizophrenia, preferably circadian programming is used to desynchronize the EEG during the patient's normal waking hours, and to synchronize the EEG at night to improve sleep. Alternatively, detection strategies such as EEG detection of beta waves over the central temporal region, and/or of abnormal sleep patterns may be employed to trigger the stimulation. The vagal stimulation may be performed continuously, periodically, or intermittently during prescribed segments of the patient's circadian cycle. For example, daytime stimulation may be periodic with a random frequency for the stimulating pulse waveform, with parameter selection for EEG desynchronization; and nighttime stimulation may employ a periodically applied pattern with parameters selected to synchronize the patient's EEG (e.g., at 90 Hz, 1 mA, 0.10 $\mu$s for the pulse waveform), alternating with desynchronizing stimuli at predetermined intervals (e.g., 100 minute separation) to produce low voltage fast (REM) activity. This regimen of vagal stimulation is programmed into the neurostimulator device.

Since the schizophrenic patient is generally unable to recognize the symptoms of the disorder, no provision is made for patient activation of the neurostimulator for treatment of this particular disorder.

The preferred range of stimulation parameters for treatment of schizophrenia are pulse width of from 0.05 to 1.5 $\mu$s, output current of from 0.1 to 5.0 mA, pulse repetition frequency of from 5 to 150 Hz, on time from 5 to 500 sec, and off time from 5 to 500 sec.

Another activation modality for daytime stimulation is to program the output of the neurostimulator to the maximum amplitude which the patient can tolerate, with cycling on and off for a predetermined period of time followed by a relatively long interval without stimulation.

For patients suffering from depression, the preferred stimulation strategy is circadian programming for nighttime stimulation to increase REM activity, and to increase synchronization of the EEG during the patient's normal waking hours. Alternatively, a strategy may be employed for EEG detection of alpha or beta waveforms, and/or EEG detection and analysis of REM activity during sleep at night, followed by large signal, infrequent stimulation when the neurostimulator is activated by the detection circuitry. As noted above, the detection may be implemented using surface or depth sensing electrodes and EEG spectral or REM analysis circuitry.

The depression patient can recognize symptoms of the disorder, and therefore may be provided with a neurostimulator which is implemented for manual activation to deliver the therapy. In the case of manual activation, the therapy applied is intended to synchronize the EEG. It is unlikely that an antidepressant effect would be achieved quickly, so the neurostimulator should be programmed to generate the stimulus for a relatively long period of time in response to manual activation. The treatment is designed, in part, to increase the activity of the vagus nerve by which to evoke a release of a greater amount of the neurotransmitters serotonin and/or norepinephrine, natural antidepressants, in the patient's brain.

Patient activation of the neurostimulator for treatment of depression or other applicable neuropsychiatric disorder may involve use of an external control magnet for operating a reed switch in the implanted device, for example. Certain other techniques of manual and automatic activation of implantable medical devices are disclosed in U.S. Pat. No. 5,304,206 to R. G. Baker, Jr. et al. (referred to herein as "the '206 patent"), which is assigned to the same assignee as the present application. According to the '206 patent, means for manually activating or deactivating the stimulus generator may include a sensor such as a piezoelectric element 31 mounted to the inner surface of the generator case and adapted to detect light taps by the patient on the implant site. One or more taps applied in fast sequence to the skin above the location of the stimulus generator in the patient's body may be programmed into the device as the signal for activation of the generator, whereas two taps spaced apart by a slightly longer time gap is programmed as the signal for deactivation, for example. The therapy regimen performed by the implanted device(s) remains that which has been pre-programmed by means of the external programmer, according to the prescription of the patient's physician in concert with recommended programming techniques provided by the device manufacturer. In this way, the patient is given limited but convenient control over the device operation, to an extent which is determined by the program dictated and/or entered by the attending physician.

A preferred range of stimulation parameters to treat depression is pulse width from 0.05 to 1.5 msec, output current from 0.1 to 5.0 mA, pulse repetition frequency from 5 to 150 Hz, on time from 5 to 500 sec, and off time from 5 to 500 sec.

The circadian programming may also be set for synchronization of sleep patterns at night (e.g., output stimulating signal of 20 Hz, 500 $\mu$s, and 2 mA, cycled at 300 seconds on and 30 seconds off).

An activation modality for daytime stimulation may be similar to that described above for treating schizophrenia, in the treatment of depression.

For borderline personality disorder, the treatment preferably is designed to modify the patient's sleep patterns toward a normal pattern. A detection strategy may be to employ implanted electrodes to sense muscle movement or actual eye movement during sleep, and to analyze the detected REM activity; or to perform EEG detection with surface or depth EEG electrodes, followed by spectral analysis of the EEG. Again, however, circadian programming of the output signal for automatic stimulation in continuous, periodic or intermittent patterns is preferred for the sake of avoiding additional invasive procedures. Usually, patient activation of the neurostimulation generator is not a viable option for the borderline personality disorder patient.

The preferred ranges of stimulation parameters for treatment of borderline personality disorder are pulse width from 0.05 to 1.5 msec, output current from 0.1 to 5.0 mA, frequency from 5 to 150 Hz, on time 5 to 1500 sec, and off time 5 to 1500 sec.

The circadian programming may employ specific patterns at night to modify REM activity for the purpose of increasing REM latency and to decrease REM intensity, tailored for each individual patient. Such a regimen of stimulation is best designed where the patient exhibits historically consistent sleep patterns, and would require defining the stimulation pattern for discrete time block during the sleep period.

If sense electrodes are to be utilized to detect onset of the disorder being treated, a signal analysis circuit would be incorporated in the neurostimulator. Upon detection of the symptom of interest of the disorder being treated, the processed digital signal is supplied to a microprocessor in the neurostimulator device, to trigger application of the stimulating signal to the patient's vagus nerve.

The principles of the invention may be applicable to selected cranial nerves other than the vagus nerve, to achieve the desired results. Hence, although certain preferred methods and modes of treating and controlling neuropsychiatric disorders through a regimen generally of cranial nerve and specifically vagus nerve stimulation directly or indirectly at a near-diaphragmatic location have been described herein, it will be appreciated by persons of ordinary skill in the art of nerve stimulation for treatment of diseases and disorders that variations and modifications may be made within the scope of the present invention as defined by the appended claims. It is therefore intended that the invention shall be limited only as required by the appended claims and by the rules of applicable law.

What is claimed is:

1. A method of treating patients with neuropsychiatric disorder, which comprises the step of stimulating a patient's vagus nerve with an electrical pulse signal applied directly or indirectly thereto at a location in the immediate vicinity of the patient's diaphragm, including selectively programming electrical and timing parameters of said electrical pulse signal according to a predetermined therapy regimen for alleviating the disorder.

2. The method of claim 1, wherein the step of stimulating the patient's vagus nerve comprises performing unilateral supra- or sub-diaphragmatic stimulation of either the left branch or the right branch of the vagus nerve.

3. The method of claim 1, wherein the step of stimulating the patient's vagus nerve comprises performing bilateral supra- or sub-diaphragmatic stimulation of the left and right branches of the vagus nerve.

4. The method of claim 1, including implanting at least one signal generator and electrodes operatively coupled thereto for generating and applying said electrical signal to the vagus nerve at said location.

5. The method of claim 1, including implanting at least one signal generator and electrodes operatively coupled thereto for generating and applying said electrical signal internally to a portion of the patient's nervous system other than the vagus nerve to indirectly stimulate the vagus nerve at said location.

6. The method of claim 1, wherein said stimulating electrical signal comprises a sequence of electrical pulses.

7. The method of claim 1, wherein the step of stimulating comprises applying said electrical signal to the vagus nerve at a location in a range of from about two to about three inches above to about two to about three inches below the patient's diaphragm.

8. The method of claim 1, wherein the step of stimulating comprises applying said electrical signal intermittently, in alternating on and off intervals according to a predetermined duty cycle.

9. The method of claim 1, wherein the step of stimulating comprises applying said electrical signal continuously.

10. The method of claim 1, wherein the step of stimulating comprises applying said electrical signal according to the patient's circadian rhythm.

11. The method of claim 1, wherein the step of stimulating comprises applying said electrical signal bilaterally and synchronously to both branches of the vagus nerve.

12. The method of claim 1, wherein the step of stimulating comprises applying said electrical signal non-invasively to a portion of the patient's nervous system other than the vagus nerve to indirectly stimulate the vagus nerve at said location.

13. The method of claim 1, including programming for initiation of the electrical stimulation by the patient upon sensing a symptom characteristic of onset of the disorder, to trigger application of said stimulating electrical pulse signal to the vagus nerve at said location.

14. A method of treating patients exhibiting neuropsychiatric disorder, including, among others, schizophrenia, depression, or borderline personality disorder, which comprises the steps of:

implanting at least one programmable electrical pulse generator in the patient together with at least one electrical lead having at least one distal nerve electrode and at least one proximal electrical connector operatively coupled to said pulse generator, implanting a distal nerve electrode of a said electrical lead on at least one branch of the vagus nerve at a location slightly above or below the patient's diaphragm, and activating said pulse generator to stimulate said branch of the vagus nerve with electrical pulses according to a programmed regimen to ameliorate the disorder.

15. The method of claim 14, including programming the implanted pulse generator to adjust the electrical parameters and application times of the pulsed electrical signal.

16. The method of claim 14, including implanting said at least one nerve electrode at said location on one of the right and left branches of the vagus nerve in a range of from approximately two inches to approximately three inches above the patient's diaphragm to approximately two inches to approximately three inches below the patient's diaphragm.

17. The method of claim 14, including implementing said pulse generator to enable patient activation thereof to stimulate said branch of the vagus nerve with electrical pulses according to said programmed regimen.

18. A method of treating patients suffering from neuropsychiatric disorder by stimulating a selected cranial nerve of the patient with an electrical signal applied to induce a signal up the nerve toward the brain from a location in the vicinity of the patient's diaphragm, including programming electrical and timing parameters of said electrical signal to alleviate said disorder.

19. The method of claim 18, including applying said electrical signal directly to the selected cranial nerve at a location substantially immediately above or below the diaphragm.

20. The method of claim 18, including applying said electrical signal internally to a portion of the patient's nervous system remote from the selected cranial nerve to indirectly stimulate the selected cranial nerve at said location.

21. The method of claim 18, wherein said stimulating electrical signal comprises a sequence of electrical pulses.

22. The method of claim 18, wherein the step of stimulating comprises applying said electrical signal to the selected cranial nerve at said location in a range of from about two to about three inches above or below the patient's diaphragm.

\* \* \* \* \*